United States Patent
Farrow et al.

(10) Patent No.: US 9,095,467 B1
(45) Date of Patent: Aug. 4, 2015

(54) TRIM-TO-FIT THERAPEUTIC COMPRESSION GARMENT SYSTEM AND METHOD

(71) Applicants: Wade P. Farrow, College Station, TX (US); Barry L. Creighton, College Station, TX (US)

(72) Inventors: Wade P. Farrow, College Station, TX (US); Barry L. Creighton, College Station, TX (US)

( * ) Notice: Subject to any disclaimer, the term of this patent is extended or adjusted under 35 U.S.C. 154(b) by 0 days.

(21) Appl. No.: 13/767,738

(22) Filed: Feb. 14, 2013

Related U.S. Application Data

(63) Continuation of application No. 13/169,240, filed on Jun. 27, 2011, now Pat. No. 8,376,977, and a continuation-in-part of application No. 12/391,051, filed on Feb. 23, 2009, now abandoned, and a continuation-in-part of application No. 12/796,579, filed on Jun. 8, 2010, now Pat. No. 8,491,514.

(60) Provisional application No. 61/478,515, filed on Apr. 24, 2011, provisional application No. 61/092,459, filed on Aug. 28, 2008, provisional application No. 61/185,129, filed on Jun. 8, 2009.

(51) Int. Cl.
  *A61F 13/00* (2006.01)
(52) U.S. Cl.
  CPC ..................... *A61F 13/00* (2013.01)
(58) Field of Classification Search
  CPC ............... A61F 2007/0042; A61F 2007/0271; A61F 7/02; A61F 13/04; A61F 13/062; A61F 2002/30014; A61F 2002/30245; A61F 2002/30354; A61F 2002/30378; A61F 2002/30387; A61F 2002/30428; A61F 2002/30

USPC ..................... 602/23–27, 60–62, 75; 128/856
  See application file for complete search history.

(56) References Cited

U.S. PATENT DOCUMENTS

| | | | |
|---|---|---|---|
| 2,687,723 A | | 8/1954 | Stern |
| 2,816,361 A | * | 12/1957 | Jobst ............................. 602/75 |
| 3,298,366 A | | 1/1967 | Moore et al. |
| 3,312,219 A | | 4/1967 | Peckham |
| 3,856,008 A | | 12/1974 | Fowler |
| 4,215,687 A | | 8/1980 | Shaw |

(Continued)

FOREIGN PATENT DOCUMENTS

| | | |
|---|---|---|
| GB | 2373444 | 9/2002 |
| WO | WO 99/36019 | 7/1999 |

(Continued)

OTHER PUBLICATIONS

3M Coban 2 Layer Compression System, Commonly Asked Questions, Feb. 13, 2007, pp. 1-3.

(Continued)

*Primary Examiner* — Michael Brown
(74) *Attorney, Agent, or Firm* — Warren M. Pate; Pate Peterson, PLLC

(57) ABSTRACT

A method of treating a condition of a patient's limb is disclosed. The method may use a compression garment wrappable about the limb and a template comprising markings showing where to trim the compression garment to fit a smaller size limb. Measurements may be taken of a circumference of the limb of the patient. Next, the template may be positioned to overlay at least a portion of the compression garment. The compression garment may then be cut or trimmed proximate a marking of the markings matching the measurement.

20 Claims, 12 Drawing Sheets

(56) References Cited

U.S. PATENT DOCUMENTS

| | | | |
|---|---|---|---|
| 4,577,622 A | 3/1986 | Jennings | |
| 4,756,026 A | 7/1988 | Pierce, Jr. | |
| 5,036,838 A | 8/1991 | Sherman | |
| 5,218,954 A | 6/1993 | van Bremmelen | |
| 5,387,183 A | 2/1995 | Jones | |
| 5,520,630 A | 5/1996 | Daneshvar | |
| 5,653,244 A | 8/1997 | Shaw | |
| 5,733,321 A * | 3/1998 | Brink | 607/111 |
| 5,741,220 A * | 4/1998 | Brink | 602/14 |
| 5,897,518 A | 4/1999 | Shaw | |
| 5,906,206 A | 5/1999 | Shaw et al. | |
| 5,918,602 A | 7/1999 | Shaw et al. | |
| 5,993,405 A | 11/1999 | Wynn | |
| 6,032,300 A | 3/2000 | Bainbridge et al. | |
| 6,109,267 A | 8/2000 | Shaw et al. | |
| 6,152,893 A | 11/2000 | Pigg et al. | |
| 6,254,554 B1 | 7/2001 | Turtzo | |
| 6,338,723 B1 * | 1/2002 | Carpenter et al. | 602/75 |
| 6,361,397 B1 | 3/2002 | Mankovitz et al. | |
| 6,415,525 B1 | 7/2002 | Watkins | |
| 6,573,419 B2 | 6/2003 | Naimer | |
| 6,613,007 B1 | 9/2003 | Reid, Jr. | |
| 6,617,485 B2 | 9/2003 | Herzberg | |
| 6,860,862 B2 | 3/2005 | Waldridge et al. | |
| 7,135,007 B2 | 11/2006 | Scott et al. | |
| 7,173,161 B1 | 2/2007 | Kandt | |
| 7,329,232 B2 | 2/2008 | Lipshaw et al. | |
| 7,513,881 B1 | 4/2009 | Grim et al. | |
| 7,867,185 B2 | 1/2011 | Lipshaw | |
| 7,942,838 B2 | 5/2011 | Farrow | |
| 8,221,340 B2 | 7/2012 | Farrow | |
| 8,251,933 B2 | 8/2012 | Farrow | |
| 8,376,977 B2 | 2/2013 | Farrow | |
| 8,491,514 B2 | 7/2013 | Farrow | |
| 8,529,483 B2 | 9/2013 | Farrow | |
| 2003/0149389 A1 | 8/2003 | Daneshvar | |
| 2003/0167548 A1 | 9/2003 | LaShoto et al. | |
| 2004/0122344 A1 | 6/2004 | Nelson et al. | |
| 2005/0113729 A1 | 5/2005 | Scott et al. | |
| 2005/0192524 A1 | 9/2005 | Lipshaw et al. | |
| 2005/0209545 A1 | 9/2005 | Farrow | |
| 2006/0010574 A1 | 1/2006 | Linnane | |
| 2007/0179421 A1 | 8/2007 | Farrow | |
| 2007/0276310 A1 | 11/2007 | Lipshaw et al. | |
| 2007/0282232 A1 | 12/2007 | Hoffman | |
| 2010/0056973 A1 | 3/2010 | Farrow et al. | |
| 2010/0312160 A1 | 12/2010 | Creighton et al. | |
| 2011/0087145 A1 | 4/2011 | Farrow et al. | |
| 2011/0125183 A1 | 5/2011 | Lipshaw et al. | |
| 2012/0010551 A1 | 1/2012 | Farrow et al. | |
| 2012/0179084 A1 | 7/2012 | Lipshaw et al. | |

FOREIGN PATENT DOCUMENTS

| | | |
|---|---|---|
| WO | WO 00/15139 | 3/2000 |
| WO | WO 2005/092401 | 10/2005 |
| WO | WO 2008/127929 | 10/2008 |
| WO | WO 2010/025186 | 3/2010 |
| WO | WO 2010/144492 | 12/2010 |
| WO | WO 2011/044500 | 4/2011 |

OTHER PUBLICATIONS

3M Coban 2 Layer Compression System, Patient Instructions, 2006, 1 page.

New 3M Coban 2 Layer Compression System Introduced for the Treatment of Edema Associated with Venous Leg Ulcers, Press Release, May 1, 2006, pp. 1-3.

Farbifoam Achilles Healer, http://www.fabrifoam.com/p-achilleshealer.html, retrieved Sep. 30, 2005.

Fabrifoam AnkleGard, http://www.fabrifoam.com/p-anklegard.html, retrieved Sep. 30, 2005.

Fabrifoam AnkleWrap, http://www.fabrifoam.com/p-anklewrap.html, retrieved Sep. 30, 2005.

Fabrifoam CarpalGard, http://www.fabrifoam.com/p-carpalgard.html, retrieved Jan. 7, 2010.

Fabrifoam ElbowGard, http://www.fabrifoam.com/p-elbowgard.html, retrieved Jan. 7, 2010.

Fabrifoam KneeGard, http://www.fabrifoam.com/p-kneegard.html, retrieved Sep. 30, 2005.

Fabrifoam MediWrap, http://www.fabrifoam.com/p-mediwrap.html, retrieved Jan. 7, 2010.

Fabrifoam NustimWrap, http://www.fabrifoam.com/p-nustimwrap.html, retrieived Sep. 30, 2005.

Fabrifoam PattStrap, http://www.fabrifoam.com/p-pattstrap.html, retrieved Jan. 7, 2010.

Fabrifoam ProWrap, http://www.fabrifoam.com/p-prowrap.html, retrieved Sep. 30, 2005.

Fabrifoam Psc, http://www.fabrifoam.com/p-psc.html, retrieved Sep. 30, 2005.

Fabrifoam SuperWrap, http://www.fabrifoam.com/p-superwrap.html, retrieved Sep. 30, 2005.

Fabrifoam WristWrap, http://www.fabrifoam.com/p-wristwrap.html, retrieved Jan. 7, 2010.

Hawkins, A New Cohesive Short-Stretch Bandage and Its Application, British Journal of Nursing, Feb. 22, 2001-Mar. 7, 2001, pp. 249-253.

Lawrance, Use of Velcro Wrap System in the Management of Lower Limb Lymphoedema/Chronic Oedema, Journal of Lymphoedema, 2008, vol. 3, No. 2, pp. 65-70.

Mayrovitz, Compression Therapy: A Summary of Important Concepts and Features, 2004, pp. 1-11.

Medassist Orthotic Products, www.medassistgp.com, 6 pages.

Mosti et al., Compression Therapy in the Treatment of Leg Ulcers, Acia Vulnologica, vol. 7, No. 3, May 2009, pp. 1-20.

Office Action mailed May 13, 2011 in connection with U.S. Appl. No. 12/391,051, pp. 1-11.

Office Action mailed Nov. 14, 2011 in connection with U.S. Appl. No. 12/391,051, pp. 1-21.

Office Action mailed Apr. 25, 2012 in connection with U.S. Appl. No. 12/391,051, pp. 1-19.

3M Coban 2 Layer Compression System Patient Instructions, 2006, 1 page.

International Preliminary Examination Report completed Jul. 24, 2006 for PCT/US2005/09483, pp. 1-7.

International Search Report and Written Opinion of the International Searching Authority mailed Jul. 6, 2005 for PCT/US2005/09483, pp. 1-12.

Supplemental Partial European Search Report completed Mar. 19, 2008 for EP 05 73 1830, pp. 1-7.

International Search Report and Written Opinion of the International Searching Authority mailed Aug. 14, 2008 for PCT/US2008/059707, pp. 1-7.

International Search Report and Written Opinion of the International Searching Authority mailed Oct. 15, 2009 for PCT/US2009/055051, pp. 1-9.

International Search Report and Written Opinion of the International Searching Authority mailed Nov. 9, 2010 for PCT/US2010/037828, pp. 1-11.

Thomas et al., An Evaluation of a New Type of Compression Bandaging System, World Wide Wounds, Sep. 2003, pp. 1-15.

Trinity Lymphedema Centers, http://www.trinitylc.com/cmpgarm1.html, 3 pages.

Understanding Compression Therapy, Medical Education Partnership, LTD, 2003, pp. 1-17.

* cited by examiner

TRIM-TO-FIT THERAPEUTIC COMPRESSION GARMENT SYSTEM AND METHOD

RELATED APPLICATIONS

This application is a continuation of U.S. patent application Ser. No. 13/169,240 filed Jun. 27, 2011, which: (1) claims the benefit of U.S. Provisional Patent Application Ser. No. 61/478,515 filed Apr. 24, 2011; (2) is a continuation-in-part of co-pending U.S. patent application Ser. No. 12/391,051 filed Feb. 23, 2009, which claims the benefit of U.S. Provisional Patent Application Ser. No. 61/092,459 filed Aug. 28, 2008; and (3) is a continuation-in-part of co-pending U.S. patent application Ser. No. 12/796,579 filed Jun. 8, 2010, which claims the benefit of U.S. Provisional Patent Application Ser. No. 61/185,129 filed Jun. 8, 2009. U.S. patent application Ser. No. 13/169,240 is hereby incorporated by reference.

BACKGROUND

1. the Field of the Invention

This disclosure relates to apparatus, methods, and systems for treating medical conditions by application of controlled compression to general and specific areas of a human or animal body.

2. The Background Art

Excessive interstitial fluid accumulation, referred to as edema, may arise from a variety of illnesses and conditions, including venous valvular insufficiency, postphlebotic syndrome, and lymphedema. Compression methods and systems control edema by reducing interstitial fluid. This in turn may increase nutrient delivery to tissues, remove waste from tissues, relieve pain from swelling, increase tissue oxygenation and promote wound healing, and decrease risk of infection. However, typical compression technologies have certain drawbacks.

For example, due to considerable variation in limb shapes and sizes, custom garments may typically be required. However, typical custom garments take time to manufacture. A delay of about one month is not uncommon between the time an order for a custom garment is placed and the time the custom garment is received by the patient. Furthermore, errors in manufacturing and measurement sometimes necessitate remanufacture of the garment or alteration of the garment to obtain a proper fit. This is very inconvenient for the patient, who needs therapeutic compression immediately and must make-do with an off-the-shelf garment or bandage until a proper custom garment can be received and utilized.

In view of the foregoing, what is needed is an improved compression garment that can be quickly and easily fit to a patient.

BRIEF SUMMARY OF THE INVENTION

In accordance with aspects of the present invention, an apparatus and method for facilitating therapeutic compression is presented. The apparatus and method may provide controlled and repeatable baseline compressions with intuitive feedback to patients. The feedback may enable a patient to safely apply proper compression, and proper compression profiles or gradients, without the need for frequent visits to clinics for trained practitioner services.

In selected embodiments, a therapeutic system in accordance with the present invention may include a compression garment coupled to one or more markings. The markings may enabling a user to alter (e.g., cut or trim) a compression garment in a manner ensuring that the desired compression profile is delivered to a patient. In general, it may be relatively expensive, time consuming, or both to apply markings directly onto a compression garment. Accordingly, in certain embodiments, a therapeutic system in accordance with the present invention may include one or more templates having the markings.

A template may enable someone to alter a compression garment without the expense and time consumption typically associated with marking directly onto a compression garment. A template may do this in one of at least two ways. In certain embodiments, a template may be formed of an inexpensive, disposable substrate upon which markings may easily be applied. For example, a template may comprise paper or plastic. Paper and plastic may each form an inexpensive, disposable substrate. Moreover, printing markings on paper or plastic may be comparatively quick and inexpensive. Alternatively, a template may be formed of a more expensive, reusable substrate whose cost may be distributed across multiple compression garments.

A method in accordance with the present invention may support customization of a compression garment to properly fit a particular patient. The method may include taking one or more measurements from a limb (e.g., foot, leg, hand, arm, etc.) of a patient. The method may further include obtaining a compression garment and obtaining a template. Obtaining a template may comprise selecting a proper template from among several templates packaged and distributed with the compression garment. The several templates may include different templates accommodating or addressing different limb lengths, limb circumferences, limb geometries or shapes, compression levels, compression profiles, or the like or combinations thereof.

Once it is obtained or selected, a template may be applied to a compression garment in any suitable manner. In selected embodiments, application of a template to a compression garment may include spreading the compression garment out flat on a surface and then overlaying the compression garment with the template. In certain embodiments, a compression garment and a template 14 may have one or more corresponding or matching fiducials enabling a user to properly position the template 14 with respect to the compression garment.

Once a proper alignment between a template and a compression garment has been achieved, a user may use the template to identify one or more locations to cut or trim the compression garment. The user may then cut the compression garment at such locations. With the cutting complete, the now customized compression garment may be donned by the patient.

BRIEF DESCRIPTION OF THE DRAWINGS

The foregoing features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF SELECTED EMBODIMENTS

Figure 1:
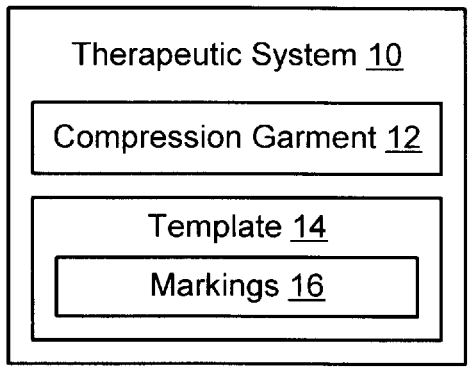
FIG. 1 is a schematic block diagram illustrating one embodiment of a therapeutic system in accordance with the present invention.

It will be readily understood that the components of the present invention, as generally described and illustrated in the drawings herein, could be arranged and designed in a wide variety of different configurations. Thus, the following more detailed description of the embodiments of the system and method of the present invention, as represented in the drawings, is not intended to limit the scope of the invention, as claimed, but is merely representative of various embodiments of the invention. The illustrated embodiments of the invention will be best understood by reference to the drawings, wherein like parts are designated by like numerals throughout.

Referring to FIG. 1, a therapeutic system 10 in accordance with the present invention may include a compression garment 12 coupled to one or more templates 14. A compression garment 12 may be constructed to deliver a desired compression profile to a patient. A template 14 may comprise a substrate for communicating (e.g., receiving and displaying) one or more markings 16 (e.g., lines 16, curves 16, slots 16, numbers 16, indicia 16, fiducials 16, text 16, or the like, or combinations thereof). Such markings 16 may enable a user (e.g., the patient, healthcare personnel, etc.) to alter the compression garment 12 in a manner ensuring that the desired compression profile is delivered to the patient. In selected embodiments, a template 14 may include markings 16 indicating where a compression garment 12 may be cut or trimmed to provide a desired compression profile to a particular patient.

Figure 2:
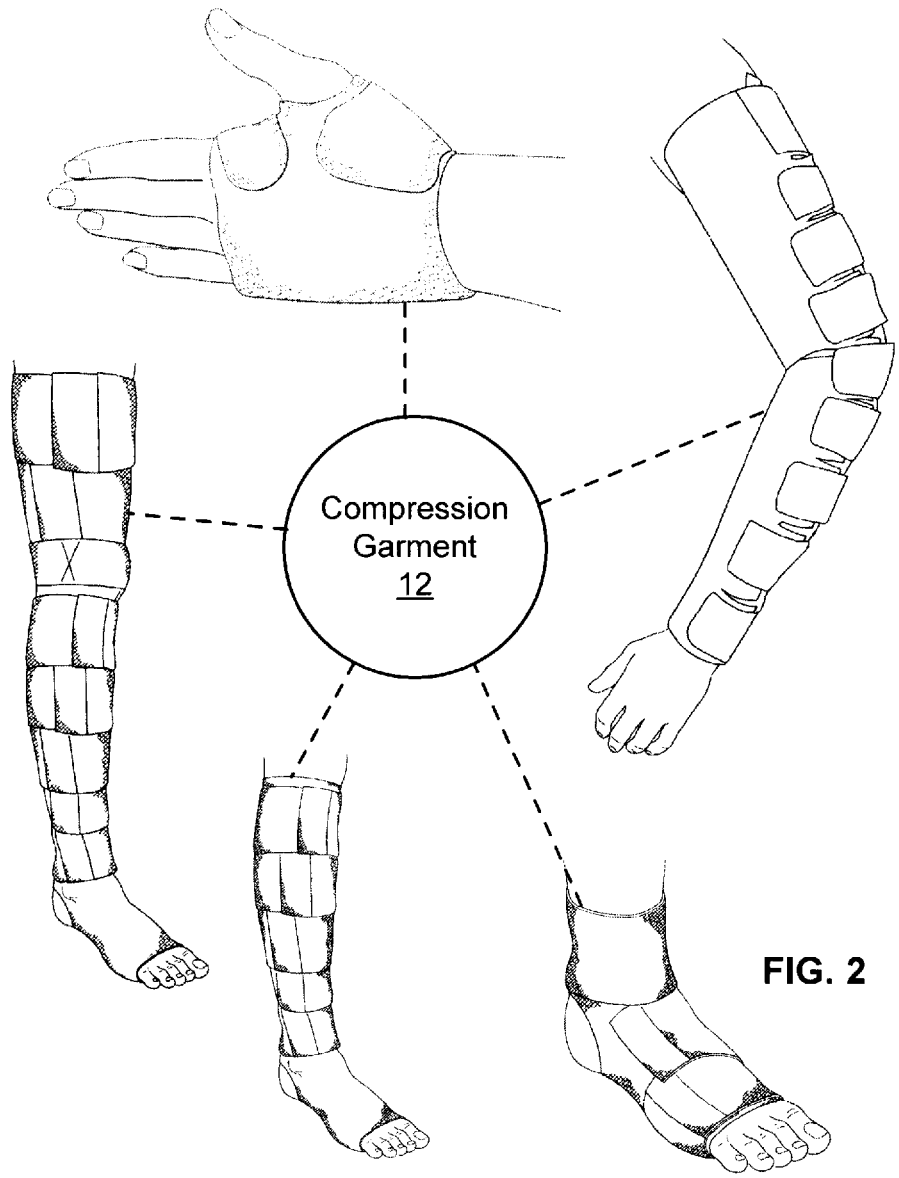
FIG. 2 is an illustration showing a non-exhaustive list of compression garments that may be used in a therapeutic system in accordance with the present invention.

Referring to FIG. 2, a compression garment 12 in accordance with the present invention may have any suitable configuration, construction, or combination thereof. Various compression garment features, materials, fabrics, physical properties, combinations, methods, bands, attachment mechanisms or closures, liners, padding, shapes, dimensions, and the like are disclosed in U.S. Patent App. Publication No. 2005/0209545 A1, U.S. Patent App. Publication No. 2007/0179421 A1, U.S. Patent App. Publication No. 2010/0056973 A1, and U.S. Patent App. Publication No. 2010/0312160 A1, each of which is hereby incorporated by reference. Any suitable embodiment, sub-combination of an embodiment, combination of embodiments, and the like of such garments, features, materials, methods, etc. may be used to produce a compression garment 12, template 14, instruction sheet, worksheet, method, or the like in accordance with the present invention.

Figure 3:
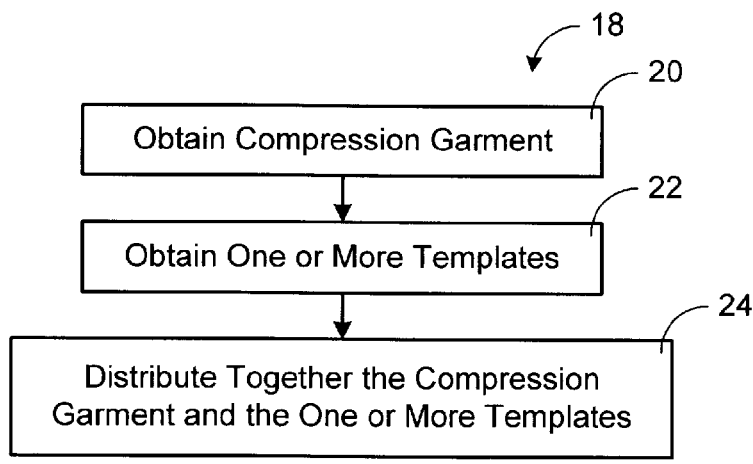
FIG. 3 is a schematic block diagram of one embodiment of a distribution method in accordance with the present invention.
Figure 4:
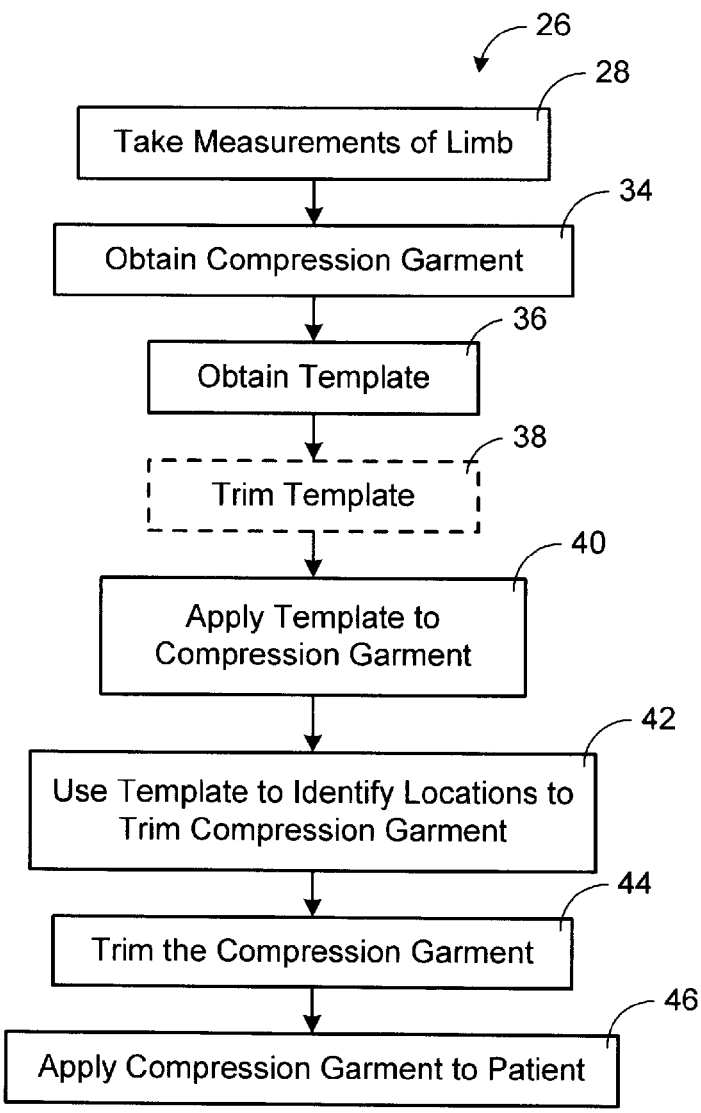
FIG. 4 is a schematic block diagram of one embodiment of a customization method in accordance with the present invention.

Referring to FIG. 3, one method 18 in accordance with the present invention may support distribution of a therapeutic system 10. The method 18 may include obtaining 20 a compression garment 12. A compression garment 12 may be obtained 20 in any suitable manner. In selected embodiments, a compression garment 12 may be manufactured by an entity executing the method 18. In other embodiments, the entity executing the method 18 may obtain 20 the compression garment 12 from some other entity or source.

In selected embodiments, when a compression garment 12 is obtained 20, it may be in a substantially completely manufactured form. For example, the compression garment 12 may be obtained 20 in such a form that it may be immediately and properly donned by at least some person. However, since a particular patient may not be shaped like that person, the compression garment 12 may be obtained 20 in a form requiring some tailoring to properly fit that particular patient. Notwithstanding such tailoring, the compression garment 12 in such embodiments may be considered substantially completely manufactured.

In other embodiments, a compression garment 12 may be obtained 20 in a partially manufactured form. That is, some, but not all, manufacturing processes necessary to produce the final compression garment 12 may have been completed. For example, the compression garment 12 may be obtained 20 in such a form that it cannot be immediately and properly donned by anyone. In such embodiments, additional work on the compression garment 12 would be require before it could be donned by any patient or source.

The method 18 may also include obtaining 22 one or more templates 14. A template 14 may be obtained in any suitable manner. In selected embodiments, a template 14 may be manufactured by an entity executing the method 18. In other embodiments, the entity executing the method may obtain 22 the template 14 from some other entity.

In general, it may be relatively expensive, time consuming, or both to apply (e.g., embroider, print, etc.) markings 16 directly onto a compression garment 12. A template 14 may enable someone to alter a compression garment 12 without that expensive or time consuming process. This may be done in one of at least two ways. In certain embodiments, a template 14 may be formed of an inexpensive, disposable substrate upon which markings 16 may easily be applied. For example, a template 14 may comprise paper or plastic. Paper and plastic may each form an inexpensive, disposable substrate. Moreover, printing markings 16 on paper or plastic may be comparatively quick and inexpensive.

Alternatively, a template 14 may be formed of a more expensive, reusable substrate whose cost may be distributed across multiple compression garments 12. A reusable template 14 may be flexible or rigid. For example, a template 14 may comprise cardboard, laminated material, polymer material, metal, or the like. Such a template 14 may be used to trim or cut multiple compression garments 12. In selected embodiments, a template 14 may include various slots formed therein. When such a template 12 is applied to a compression garment 12, one or more slots or edges may guide a cutting tool (e.g., roller knife or cutting blade) traveling therealong or therewithin along a particular path to provide the desired alteration to the compression garment 12. Accordingly, the template 14 itself may not be altered during use and may be applied to multiple compression garments 12.

A template 14 may form a single piece. For example, a template 14 may be formed from a single sheet of paper or plastic. Alternatively, a template 14 may be precut or preassembled from one or more pieces. For example, a template 14 may comprise multiple, overlapping pieces of paper, plastic, or the like.

Once the compression garment 12 and the one or more templates 14 have been obtained 20, 22, they may be distributed 24 together. For example, a substantially completely manufactured or partially manufactured compression garment 12 may be packed with one or more templates 14 and shipped to a patient, health care provider, medical supply company, or the like. In certain shipments or packages (e.g., shipments or packages comprising exclusively disposable templates 14), the ratio of templates 14 to compression garments 12 may be greater than or equal to one. In other shipments or packages (e.g., shipments or packages comprising exclusively reusable templates 14), the ratio of templates 14 to compression garments 12 may be less then one.

In selected embodiments, a compression garment 12 may distributed 24 with a "soft copy" of a template 14. A soft copy may comprise a digital file (e.g, PDF file, JPEG file, or the like) that may be viewed, projected, printed, plotted, or the like to support the desired alteration to the compression garment 12. A soft copy of a template 14 may be stored on a non-transitory, computer-readable medium (e.g., CD ROM) distributed 24 with a compression garment 12. Alternatively, a compression garment 12 may be distributed 24 with information linking a compression garment 12 to a soft copy of a template 14. For example, a compression garment 12 may be distributed 24 with an address (e.g., Internet address, email address) from which the soft copy, customization instructions, a customization demonstration, or some combination thereof may be obtained (e.g., requested, viewed, downloaded, printed, etc.) by a user.

Referring to FIGS. 4-7, one method 26 in accordance with the present invention may support customization (e.g., on-site or on-demand customization) of a compression garment 12 to properly fit a particular patient. The method 26 may include taking 28 one or more measurements from a limb (e.g., foot, leg, hand, arm, etc.) of a patient. Accordingly, in selected embodiments, a compression garment 12 may be linked to, accompanied by, or distributed 24 with materials (e.g., instructions) assisting a user in taking 28 the necessary measurements.

For example, a compression garment 12 may be linked to, accompanied by, or distributed 24 with a worksheet 30. A worksheet 30 may inform a user how and where to take 28 measures, given the nature of the corresponding compression garment 12 or garments 12. Different worksheets 30 may correspond to different compression garments 12. For example, one worksheet 30*a* may correspond to a compression garment 12 for an arm, another worksheet 30*b* may correspond to a compression garment 12 for a lower leg, another worksheet 30*c* may correspond to a compression garment 12 for an entire leg, etc. A worksheet 30 may provide locations 32 for a user to record the measurements taken 28. In selected embodiments, a worksheet 30 may guide a user in selecting which template 14 to use to properly customize the compression garment 12.

A customization method 26 in accordance with the present invention may further include obtaining 34 a compression garment 12 and obtaining 36 a template 14. In selected embodiments, obtaining 36 a template 14 may comprise selecting a proper template 14 from among several templates 14 (e.g., from among several templates 14 packaged and distributed 24 with the compression garment 12). The several templates 14 may include different templates 14 accommodating or addressing different limb lengths, limb circumferences, limb geometries or shapes (e.g., very wide calf muscles, large skin lobules, etc.), compression levels, compression profiles, or the like.

When selecting a template 14 from among several templates 14, each template 14 of the several need not be universally applicable. For example, each template 14 does not need to have markings 16 pertaining to every potential modification of a corresponding compression garment 12. Rather, each template 14 may comprise markings 16 corresponding to a limited set of potential modification. Accordingly, no template 14 needs to have an excessive or confusing quantity or arrangement of markings 16. Collectively, however, the several templates 14 may support all or a significant portion of desired modifications to the corresponding compression garment 12.

In selected embodiments, the several templates 14 may constitute an array of sizes (e.g., extra small, small, medium, large, extra large, extra extra large, or some combination thereof). In such embodiments, a template 14 corresponding to a particular size may focus on a limited set of modifications surrounding that particular size. For example, an extra small template 14 may provide an array of markings 16 for tailoring a compression garment 12 to a patient limb that may be characterized as extra small. Conversely, an extra large template 14 may provide an array of markings 16 for tailoring a compression garment 12 to a patient limb that may be characterized as extra large.

Alternatively, or in addition thereto, the several templates 12 may support customization of a compression garment 12 to provide different levels of compression. For example, one template 14 may correspond to a garment 12 applied at about 100% stretch (e.g., substantially at end stretch, maximal stretch, or near the end of its elastic range), while one or more other templates 14 may correspond to a garment 12 applied at less than 100% stretch (e.g., 75% stretch, 50% stretch, or the like). A template 14 may also enable or support creation of a compression garment 12 to be applied with more stretch in some areas and less in others. For example, a template 14 may enable or guide a user to customize a compression garment 12 so that it is applied at 75% stretch around a joint area for better comfort, but applied at 90-100% stretch around a calf muscle for better calf muscle pump activation.

In selected embodiments, one template 14 may tailor a compression garment 12 to provide compression of about 20-30 mm Hg. Another template 14 may tailor a compression garment 12 to provide compression of about 30-40 mm Hg.

One or more templates 14 may enable a user to tailor a compression garment 12 to any of the standard compression levels used in the United States (e.g., 8-15 mm Hg, 15-20 mm Hg, 20-30 mm Hg, 30-40 mm Hg, 40-50 mm Hg, or higher). One or more templates 14 may enable a user to tailor a compression garment 12 to any other standard compression levels (e.g., compression levels associated with the German Raul Standard, United Kingdom standard, French standard, or the like).

Through the use of templates 14, the number of compression garments 12 stocked by an entity (e.g., clinic, hospital, supplier or distributor of durable medical equipment (DME), or the like) may be significantly reduced. The entity may stock a particular compression garment 12 that may be trimmed to various sizes. Accordingly, the entity need not stock multiple sizes of the particular compression garment. Moreover, by obtaining 36 (e.g., selecting) a proper template 14, the markings 16 provided thereby may be simplified and focused so as not to confuse a user.

There may be some reluctance of a user to trim a compression garment 12. This reluctance may be based on a fear that the user will not cut the compression garment 12 properly, thereby wasting the compression garment 12 and the money spent thereon. Accordingly, in selected embodiments, once a template 14 has been obtained 36, it may be trimmed 38. A trimmed template 14 may be applied to the corresponding limb, thereby providing a proof of the process and the measurements taken 28. In selected embodiments, a template 14 may have one or more regions having a sticky backing enabling the template 14 to be placed around a patient's limb and stay there for sizing verification. After which, the template 14 may be removed from the limb.

By trimming 38 a template 14, a user may feel more comfortable trimming the actual compression garment 12 and lower the risk of trimming it incorrectly. In selected embodiments, a compression garment 12 may be distributed 24 with multiple copies of the same template 14. Accordingly, should a user trim 38 one such template 14 incorrectly, a whole template 14 may still be available for use.

A template 14 may be applied 40 to a compression garment 12 in any suitable manner. The manner of application 40 may depend on the characteristics of the compression garment 12, the template 14, or both. In selected embodiments, application 40 of a template 14 to a compression garment 12 may include spreading the compression garment 12 out flat on a surface and then overlaying the compression garment 12 with the template 14.

In certain embodiments, a compression garment 12 and a template 14 may have one or more corresponding or matching fiducials. A fiducial may comprise a location reference. Matching (e.g., overlaying) fiducials between a compression garment 12 and a corresponding template 14 may enable a user to properly position the template 14 with respect to the compression garment 12. Suitable fiducials may include seams, points, lines, curves, boundaries, edges, labels, notches, and the like.

For example, in selected embodiments, the shape (or some portion thereof) of a template 14 may match the shape or boundary profile of a compression garment 12. Accordingly, alignment of one or more edges on a template 14 with corresponding edges on a compression garment 12 may ensure that the two components 12, 14 are properly aligned with respect to one another.

A template 14 may be transparent, semi-transparent, or opaque. In selected embodiments, a template 14 that is transparent or semi-transparent may enable a user to more easily orient a template 14 properly with respect to a compression garment 12 (e.g., align a fiducial on a template 14 with a corresponding fiducial on a compression garment 12). Alternatively, or in addition thereto, a template 14 may include one or more regions configured to adhere to at least a certain degree to a compression garment 12. Such regions may resist relative movement between a template 14 and a compression garment 12 during customization (e.g., trimming) of the compression garment 12. In selected embodiments, a template 14 may be backed with a sticky material. In other embodiments, a template 14 may be statically charged, include one or more regions of hook-and-loop type material (e.g., the hook portion of such material), or the like to provide a desired adhesion.

In certain embodiments, a customization method 26 in accordance with the present invention may be performed at a particular location (e.g., clinic, hospital, place of business of a supplier or distributor of DME, or the like) with sufficient frequency to merit selected structures facilitating that method 26. Such locations may be considered customization sites. Reusable templates 14 may be well suited for use at a customization site. Alternatively, or in addition thereto, a customization site may include a computer programmed to receive the measurements taken 28 from a patient and output or identify an appropriate template 14. In selected embodiments, the appropriate template 14 may be output in a printing process (e.g., printing or plotting on a substrate such as paper, plastic, or the like). In certain embodiments, the appropriate template 14 may be printed or plotted directly onto a corresponding compression garment 12.

Alternatively, the appropriate template 14 may be output (e.g., applied 40 to a compression garment 12) in exclusively a visual manner. For example, a template 14 may be projected onto a compression garment 12. This may be accomplished using a digital projector (e.g., video projector) or an overhead projector, a computer display screen or monitor, or the like. A user may move the compression garment 12 until it is properly aligned with the projected template 14. For example, a user may move the compression garment 12 until one or more fiducials on the compression garment 14 align corresponding fiducials on the projected template 14.

Once a proper alignment between a template 14 and a compression garment 12 has been achieved, a user may use 42 the template 14 to identify one or more locations to cut or trim the compression garment 12. The user may then cut 44 the compression garment 12 at such locations. With the cutting 44 complete, the now customized compression garment 12 may be applied 46 to a corresponding patient (e.g., donned by the corresponding patient). In selected situations or applications, a customization method 26 in accordance with the present invention may be applied more than once to a particular compression garment 12 or for a particular patient. For example, following a period of successful compression treatment, the edema within a limb may be reduced. Accordingly the dimensions or shape of the limb may have changed since a first application of the method 26. The effectiveness of the compression garment 12 may be reduced. Thus, the method 26 may be repeated to customize the compression garment 12 to the new (e.g., reduced) dimensions, shape, or the like of the patient. In certain embodiments, a disposable (e.g., paper) template 14 used in the first application of the method 26 may be used in one or more subsequent applications of the method 26.

Figure 8:
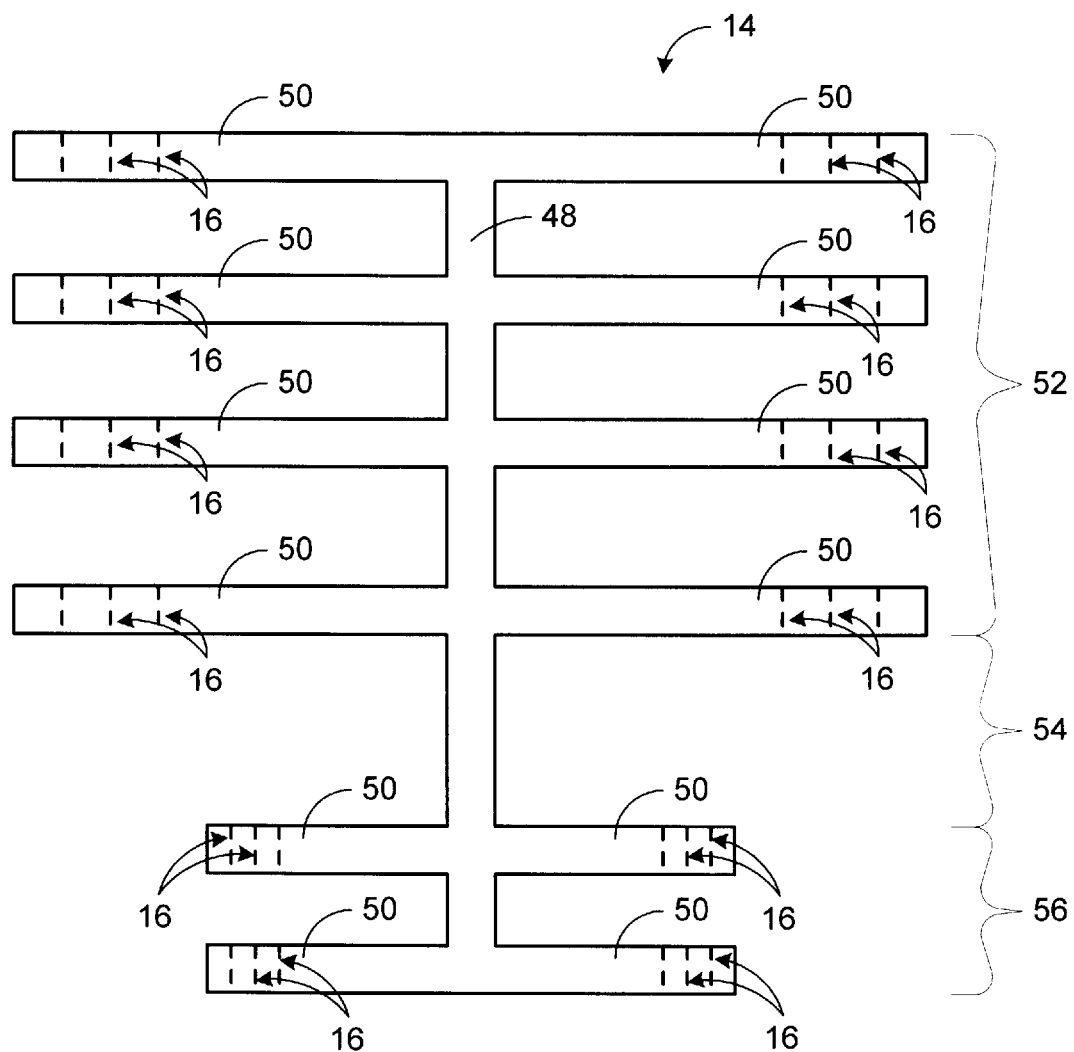
FIG. 8 is a plan view of one embodiment of a template in accordance with the present invention for customizing a compression garment for the lower leg and foot of a patient.

Referring to FIG. 8, in selected embodiments, a template 14 may have a "fishbone" type design comprising a central spine 48 and multiple branches 50 extending from either side thereof. The various sections or portions of the template 14 may correspond to different portions of a limb. For example, a first portion 52 may correspond to a lower leg, a second portion 54 may correspond to a heel, and a third portion 56 may correspond to a foot. Such a template 14 may be well suited for use with a compression garment 12 comprising overlapping bands. Markings 16 on the ends of the various branches 50 may identify various locations where the bands may be cut or trimmed.

Referring to FIGS. 9-14, templates 14 in accordance with the present invention may include markings 16 of various kinds. For example, templates 14 may include textual (e.g., number) markings 16a, cut or trim lines 16b (e.g., lines identifying where to cut or trim a corresponding compression garment 12), fiducials 16c (e.g., edges 16c and markings 16c or text 16c showing where to positioning a template 14 or corresponding garment 12 on a patient), dividing lines 16d (e.g., lines identifying where to make certain dividing or partial dividing cuts), hash marks 16e (e.g., markings communicating incremental distances), and the like.

In selected embodiments, textual markings 16a may correspond to measurements taken 28 from a patient. Accordingly, if a particular circumference taken 28 from a patient has a certain value (e.g., 20 cm), then the user may cut 44 or trim 44 a corresponding portion of a corresponding compression garment 12 along a line 16b associated with a "20" textual marking 16a. Should a measured value fall between two textual markings 16a, the user may be instructed to use (e.g., cut along the line 16b corresponding to) the higher value of the two. Alternatively, the user may be instructed to make approximations (e.g., trim between the lines 16b or other fiducial markings 16c).

Fiducials 16c and other markings 16 may be used to align a compression garment 12 to anatomical landmarks on a patient. They may also be used to help determine where, how, how far, or the like to stretch a compression garment 12 during application to get a proper therapeutic effect. For instance, using a 25% overlap of a compression garment 12 onto itself, after proper trimming and application, may allow the compression garment 12 to work properly to prevent any exacerbation of the edema.

Fiducials 16c and other markings 16 may be used to identify locations on a compression garment 12 where padding (e.g., spacer fabric, foam, foam with adhesive backing, or the like) may be added. Alternatively, or in addition thereto, the markings 16 may communicate a suitable or preferred size or geometry of the padding. For example, the markings 16 may communicate a location and desired channel shape for padding located proximate the back of the knee to facilitate lymph drainage, increase comfort, or the like.

In selected embodiments, fiducials 16c and other markings 16 may identify more than just locations where a compression garment 12 may be shortened or otherwise trimmed. For example, markings 16 may identify one or more locations where small slits (e.g., slits about one centimeter in length) may be formed in the compression fabric of a corresponding compression garment 12. Such slits acting alone or in a desired arrangement or pattern may permit greater stretching of a compression fabric, alter compression characteristics of compression garment 12, or the like.

Fiducials 16c and other markings 16 on a template 14 may be transferred to a compression garment 12 to illustrate or communicate proper compression levels once the garment 12 is applied. By building complicated algorithms and processes into a template 14, a user or trimmer of a compression garment 12 in accordance with the present invention may avoid such complexities.

Figure 5:
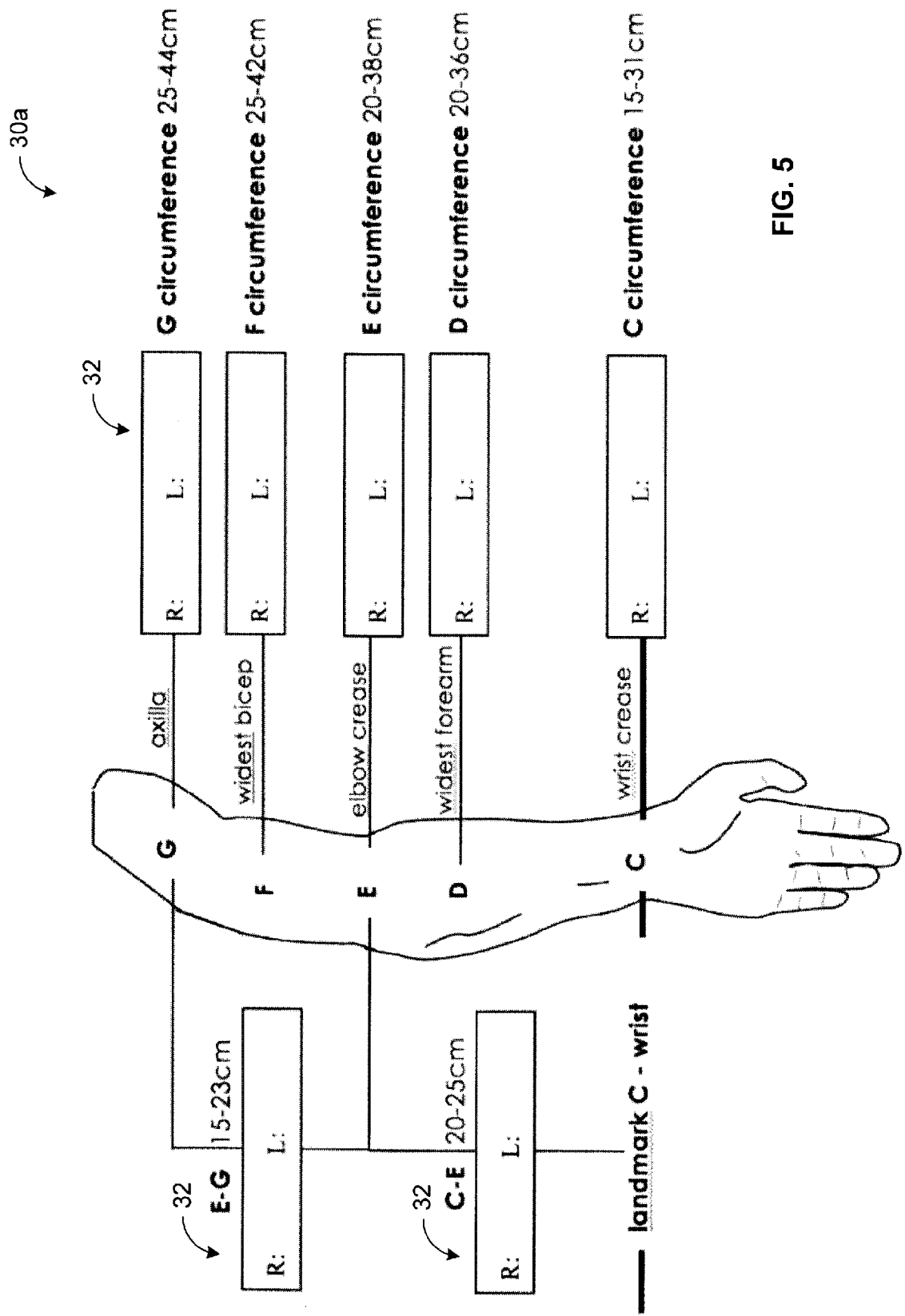
FIG. 5 is an illustration showing one embodiment of a worksheet in accordance with the present invention for recording measurements of a patient's arm.
Figure 6:
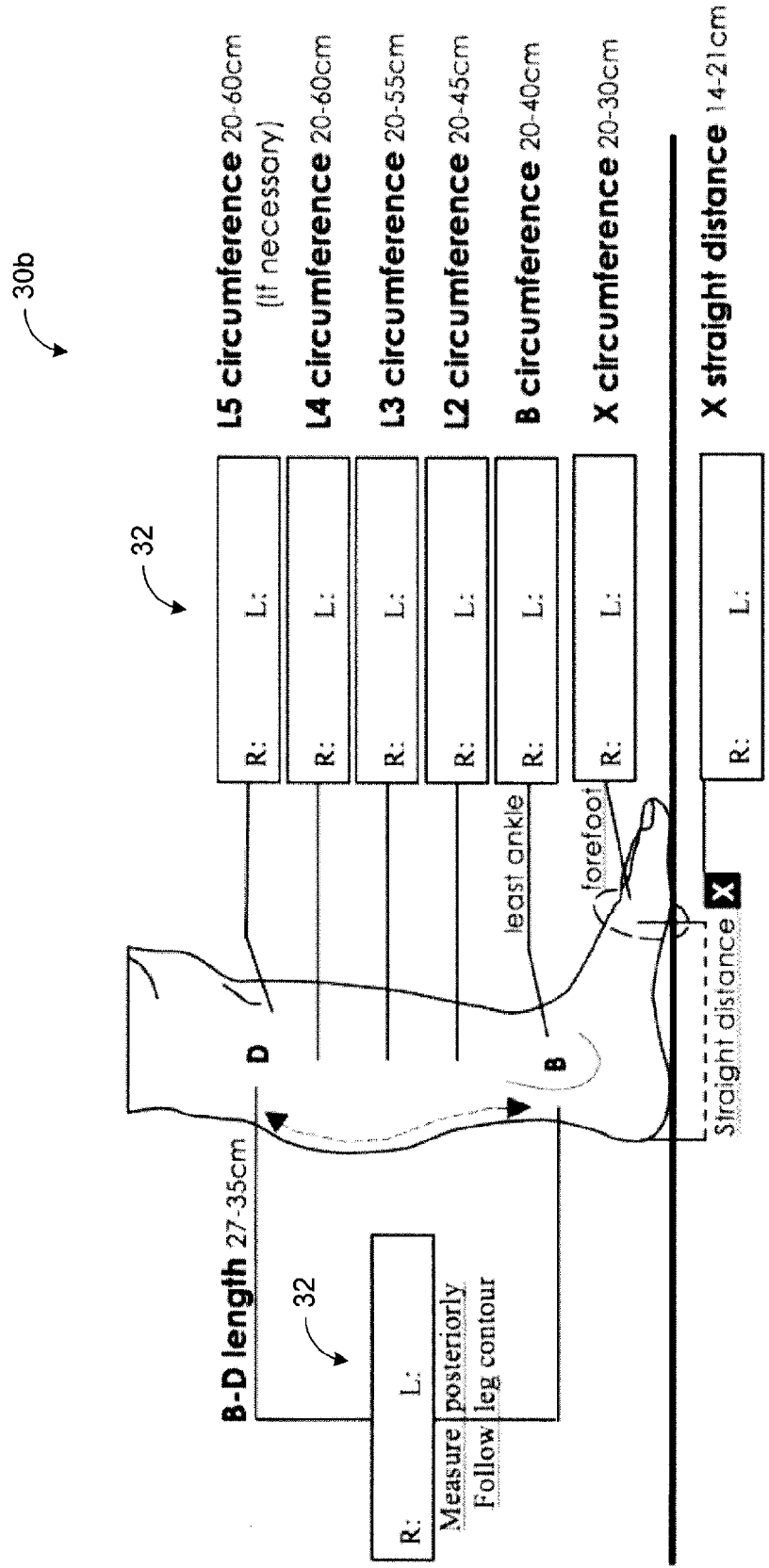
FIG. 6 is an illustration showing one embodiment of a worksheet in accordance with the present invention for recording measurements of a patient's lower leg.
Figure 9:
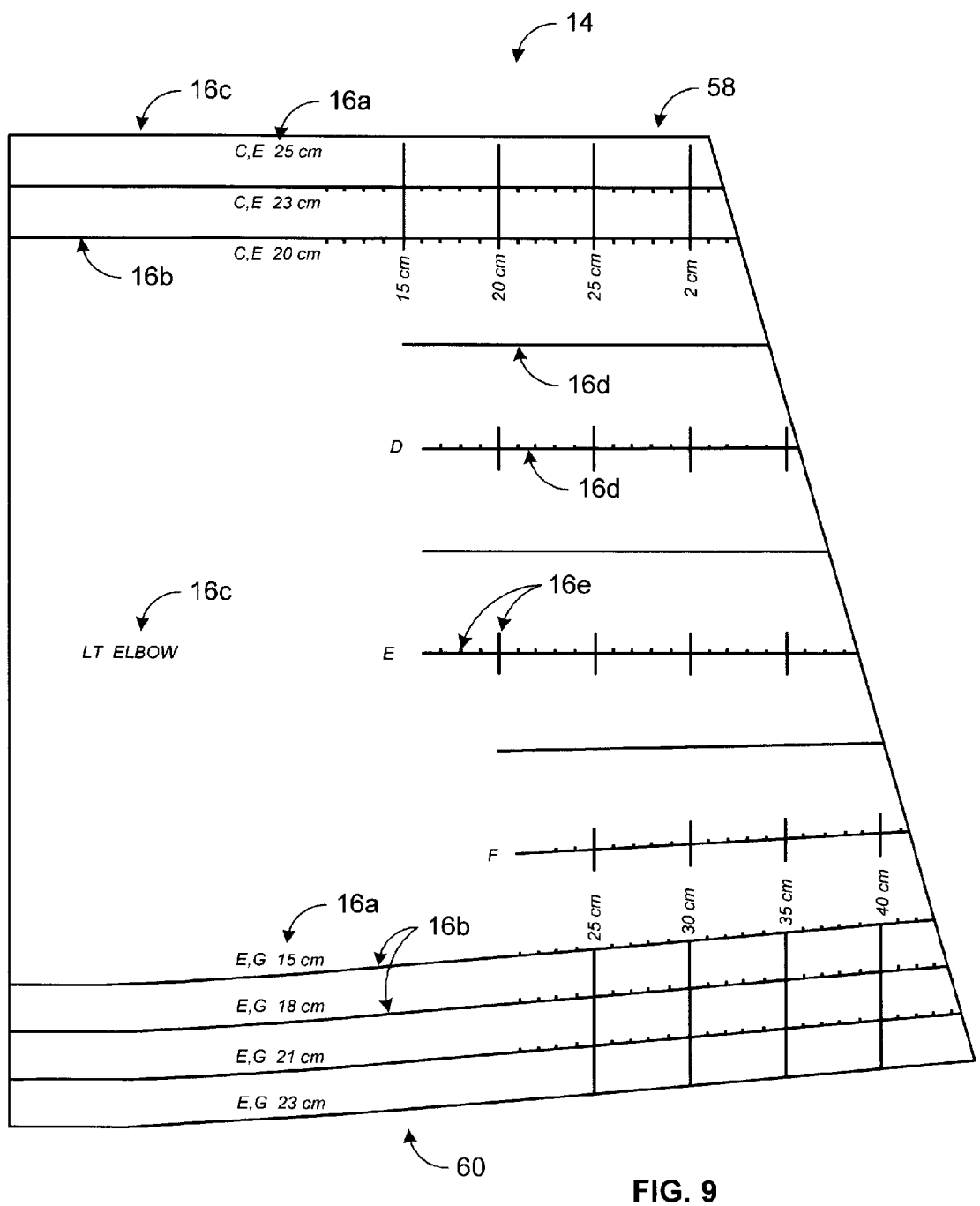
FIG. 9 is a plan view of one embodiment of a template in accordance with the present invention for customizing a compression garment for the arm of a patient.

Referring to FIG. 9, after taking and recording various measurements on the worksheet 30a of FIG. 5, a user may be ready to trim a compression garment 12 for an arm. Accordingly, a user overlay or otherwise align the compression garment 12 with an appropriate template 14. Using the template 12, a user may trim a distal end 58 of the compression garment 12 according to a measured distance "C to E" identified on the worksheet 30a. A user may trim a proximal end 60 of the compression garment 12 according to a measured distance "E to G" identified on the worksheet 30a.

Once the distal and proximal ends 58, 60 are trimmed, a template 14 may assist a user in identifying various lines (e.g., edges 16c, dividing lines 16d, or the like) corresponding to the worksheet 30a. In the embodiment of FIG. 9, the distal edge of the compression garment 12 may form or define line "C," while the proximal edge of the compression garment 12 may form or define line "G." Intermediate lines "D," "E," and "F" may be positioned as noted on the template 14.

Using the measurements recorded on the worksheet 30a and the hash marks 16e of the template 14, a user may identify appropriate locations on the various lines C, D, E, and F. In trimming the compression garment 12, a user may "connect the dots," crossing each of the various lines C, D, E, and F at the appropriate locations. A user may then follow one or more dividing lines 16d and cut therealong some distance (e.g., about three or four centimeters) into the body or interior of the compression garment 12. The compression garment 12 may then be ready for donning by a patient. Since the compression garment 12 has been customized using measurements collected directly from the patient, providing a specific overlap distance as the compression garment 12 is wrapped around a limb (e.g., the patient's arm) may ensure that a desired or prescribed compression is applied to the limb.

Figure 10:
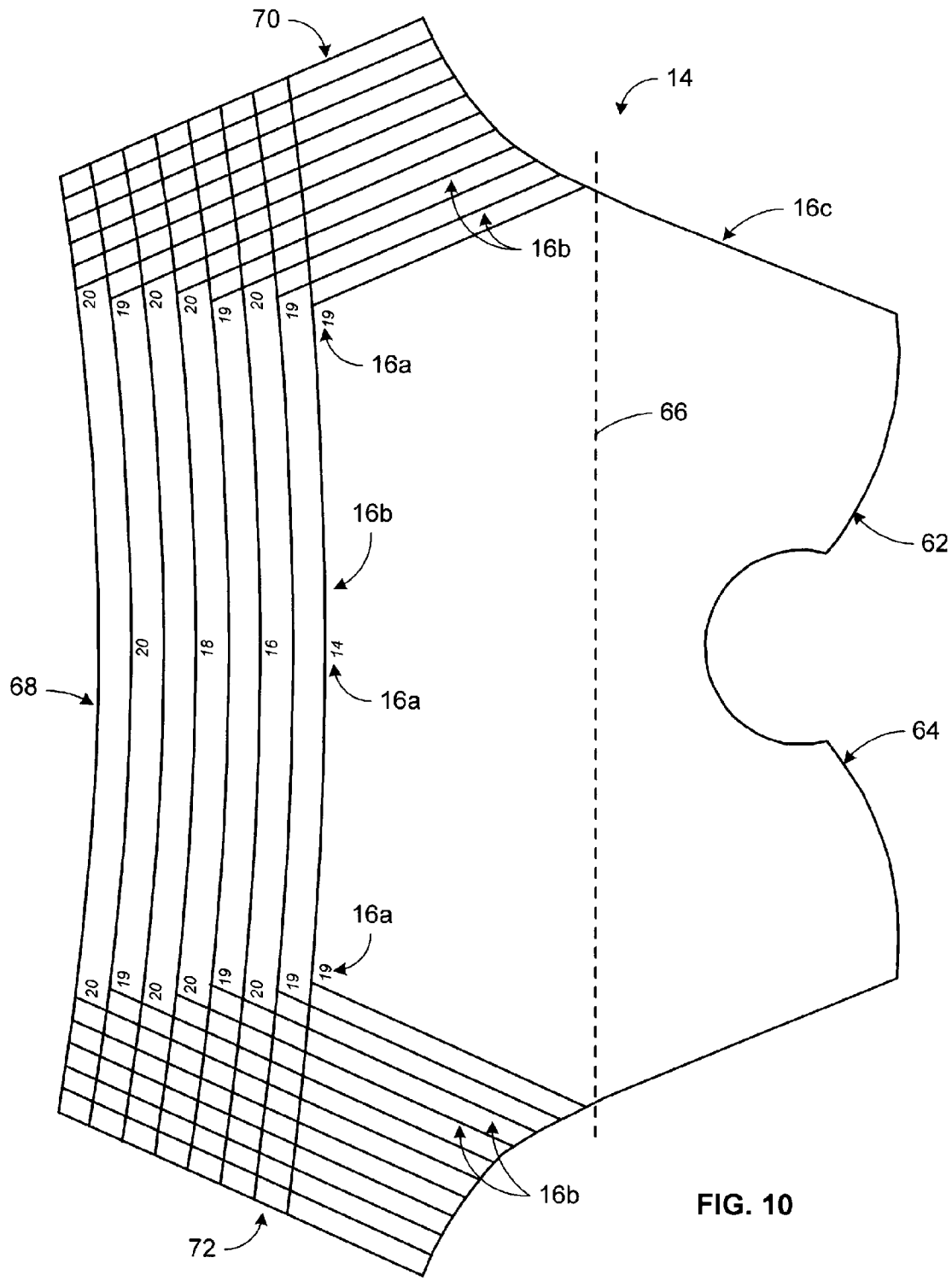
FIG. 10 is a plan view of one embodiment of a template in accordance with the present invention for customizing a compression garment for the foot of a patient.
Figure 11:
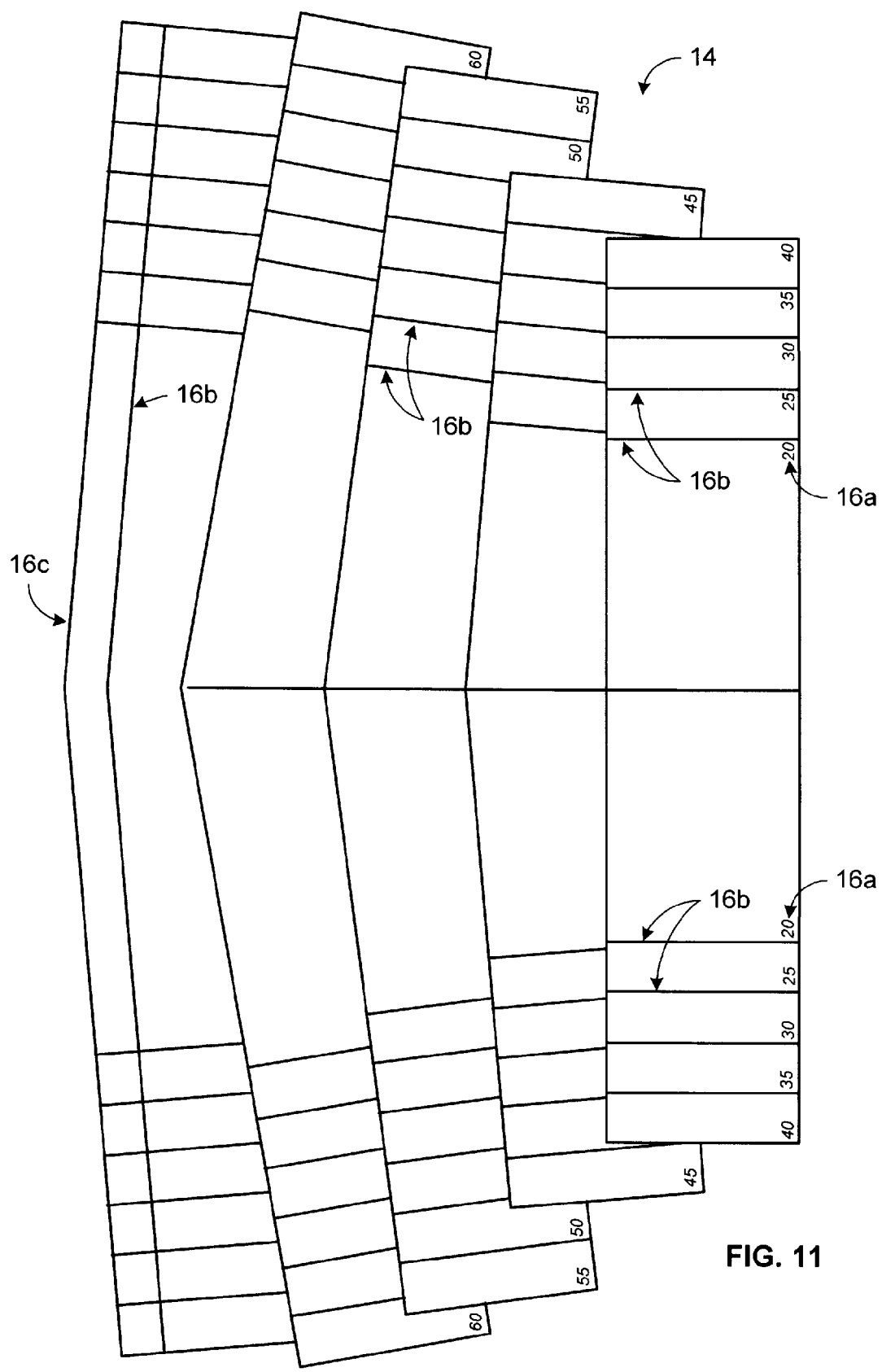
FIG. 11 is a plan view of one embodiment of a template in accordance with the present invention for customizing a multi-band compression garment for the lower leg of a patient.
Figure 12:
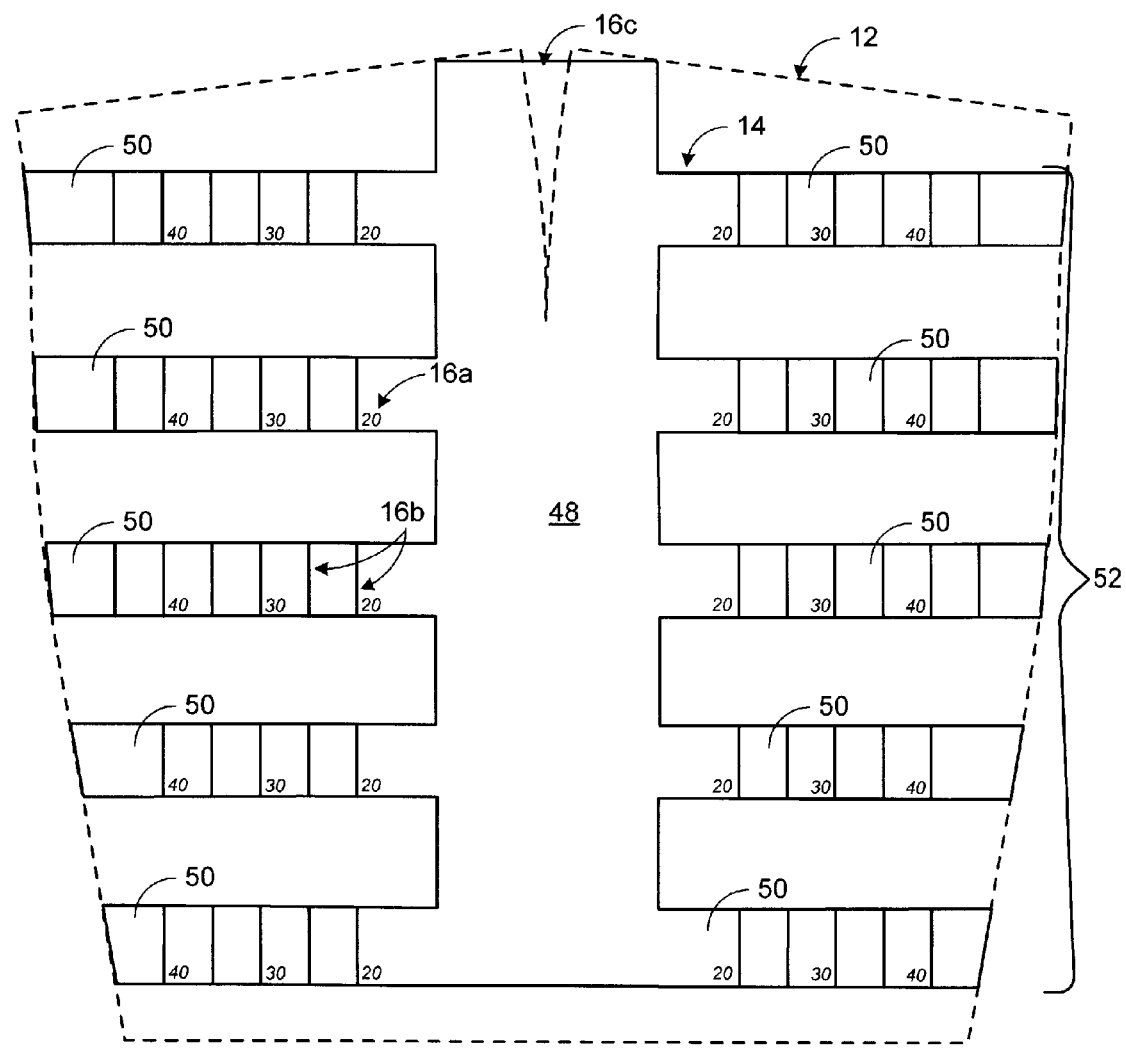
FIG. 12 is a plan view of an alternative embodiment of a template in accordance with the present invention overlaying a compression garment (shown with dashed lines) for the lower leg of a patient.

Referring to FIG. 10, in selected embodiments, a manufactured compression garment 12 may not easily lay flat. For example, assuming that the template 14 shown in FIG. 10 were the fabric of a compression garment 12, a manufacturing process may connect (e.g., sew) a first edge 62 to a corresponding second edge 64 to form a heel cup. So connected, the resulting compression garment 12 may not easily lay flat for application of a template 14 thereto.

In such embodiments, a partial template 14 may be used. A partial template 14 may cover only those portions of the compression garment 12 that need to be trimmed, that lay flat, or some combination thereof. In the illustrated embodiment, a partial template 14 may be formed by omitting certain portions of the template 14 (e.g., portions to the right of the illustrated line 66). Alternatively, a user may simply focus on properly overlaying a template 14 on certain of the portions of a compression garment 12 that need to be trimmed. Thus, a user need not have complete alignment at all times of all portions of a template 14 with a corresponding compression garment 12.

Figure 7:
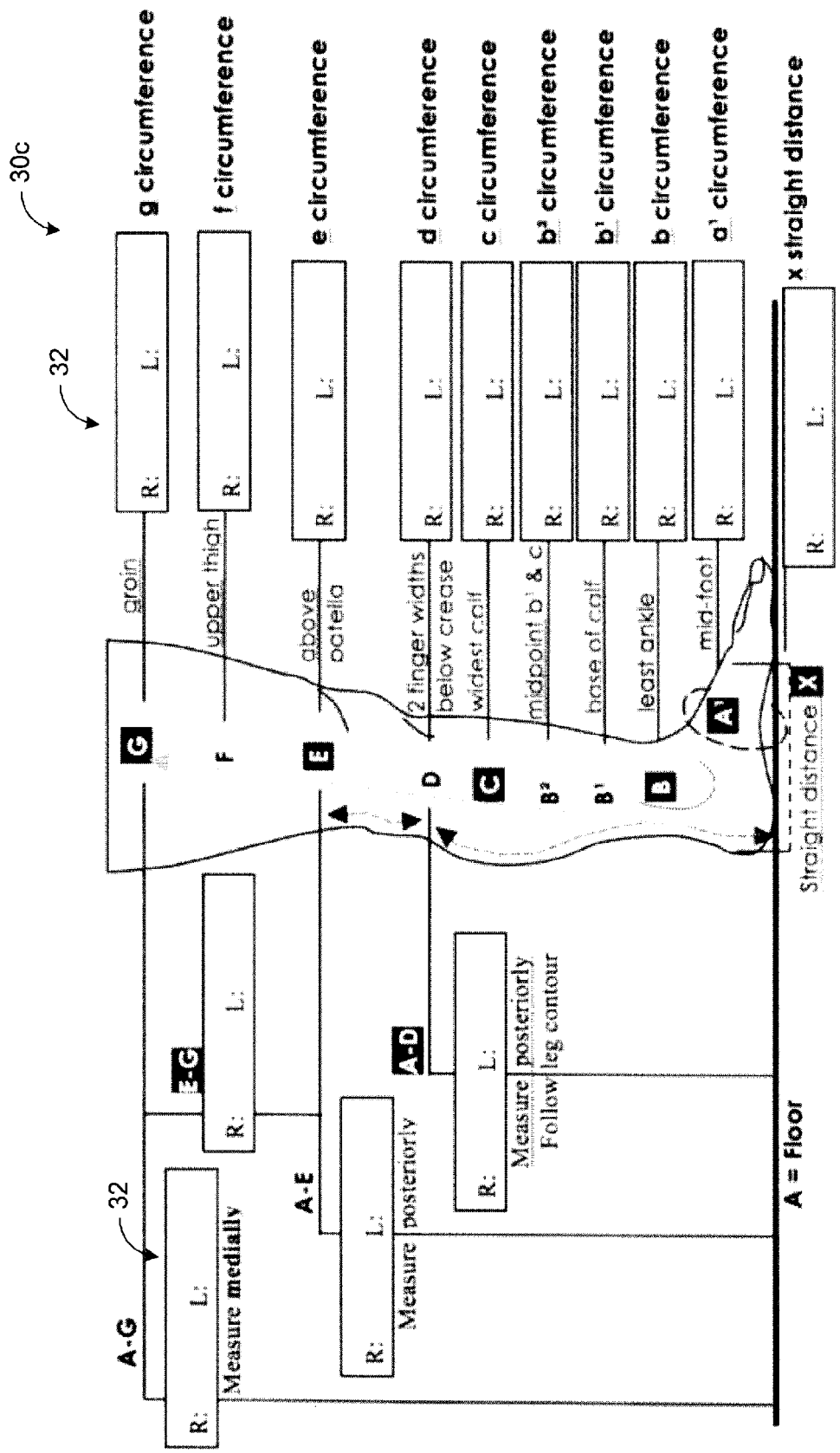
FIG. 7 is an illustration showing one embodiment of a worksheet in accordance with the present invention for recording measurements of a patient's leg.

After taking and recording various measurements noted on the foot portion of worksheet 30c of FIG. 7, a user may be ready to trim a compression garment 12 for a foot. Accordingly, a user may align (e.g., partially overlay) the compression garment 12 with an appropriate template 14. Using the template 14, a user may trim a third edge 68 of the compression garment 12 according to a measured distance "X" identified on the worksheet 30c. A user may then trim fourth and fifth edges 70, 72 according to a measured circumference "A'" identified on the worksheet 30c. The location of the trimmed third edge 68 may determine where (e.g., at what value) corresponding measurements for the fourth and fifth edges 70, 72 begin.

Once the third, fourth, and fifth edges 68, 70, 72 are properly trimmed, the compression garment 12 may be ready for donning by a patient. Again, since the compression garment 12 has been customized using measurements collected directly from a patient, providing a specific overlap distance as the compression garment 12 is wrapped around a limb (e.g., the patient's foot) may ensure that a desired or prescribed compression is applied to the limb.

Figure 13:
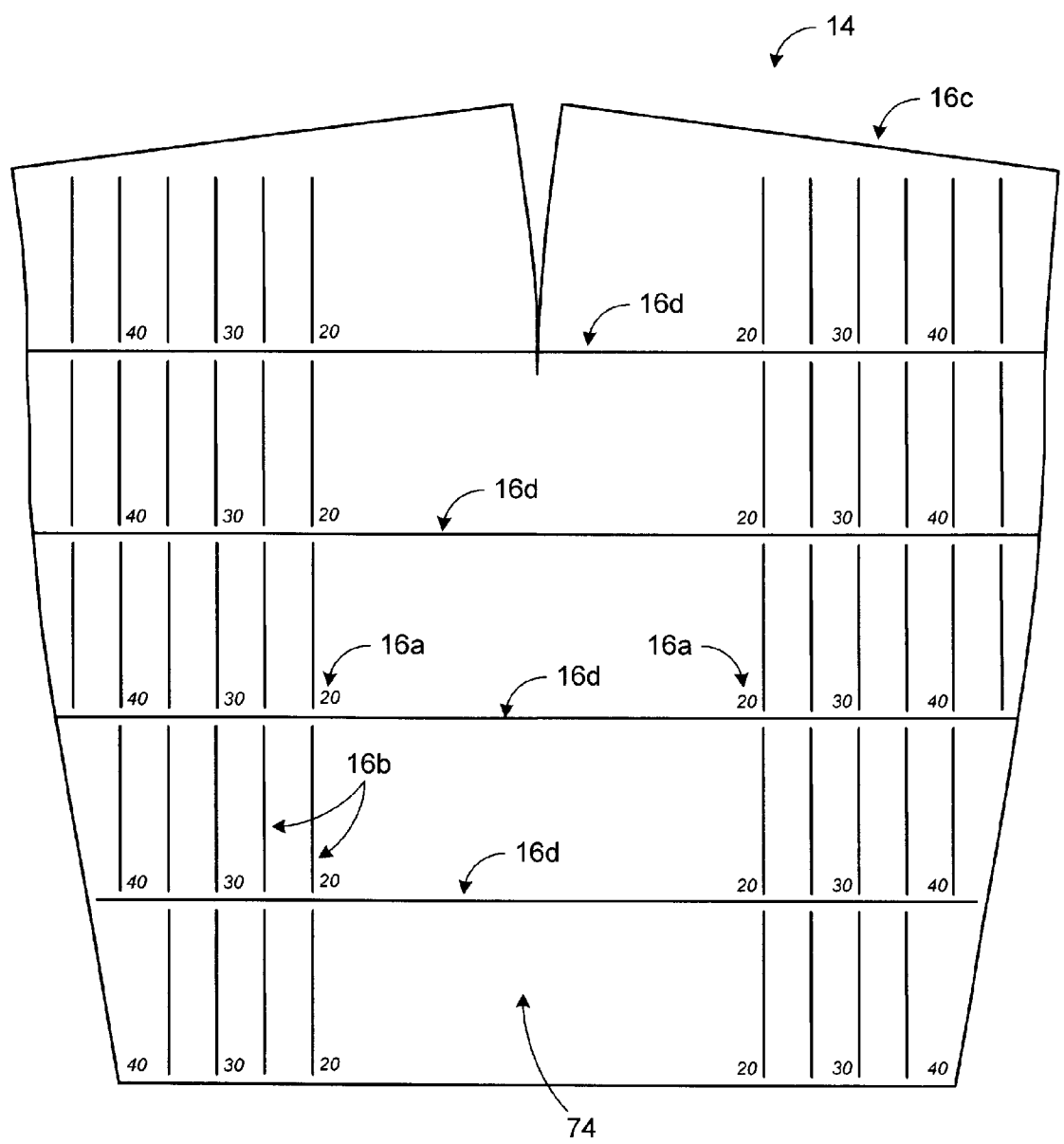
FIG. 13 is a plan view of another alternative embodiment of a template in accordance with the present invention for customizing a compression garment for the lower leg of a patient.
Figure 14:
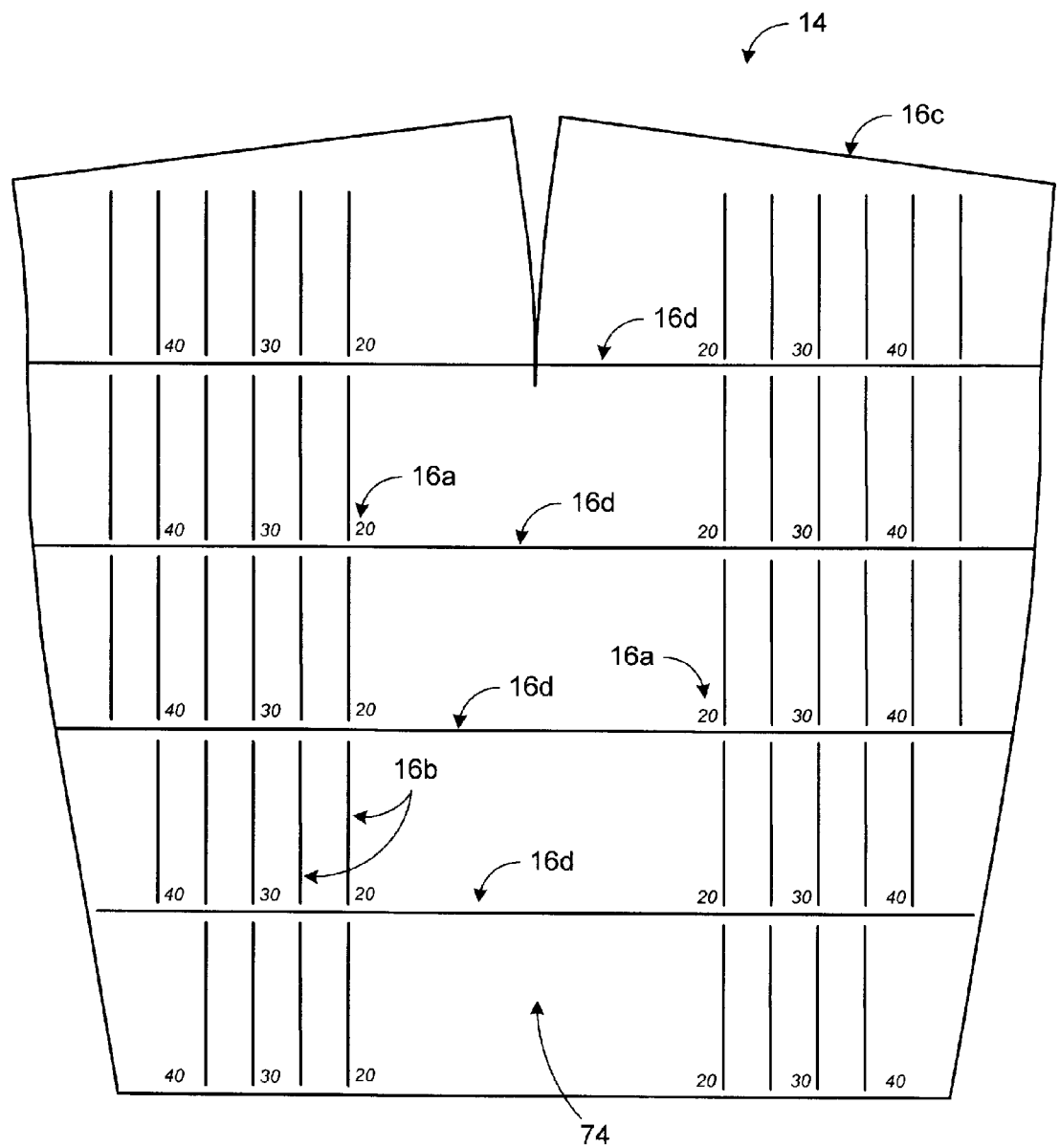
FIG. 14 is a plan view of another alternative embodiment of a template in accordance with the present invention for customizing a compression garment for the lower leg of a patient, the template having the same exterior border as the template of FIG. 13 but with different markings to accommodate a different sized patient, a different compression level, or the like or some combination thereof.

Referring to FIGS. 13 and 14, in selected embodiments, a template 14 may include multiple sets of markings 16. For example, a first set of markings 16 may correspond to a first compression level or profile, while a second set of markings 16 may correspond to a second compression level or profile. The various sets of markings 16 may be distinguishable. For example, a first set of markings 16 may be in a first color, while a second set of markings 16 may be in a second, different color.

Alternatively, each template 14 may include only one set of markings 16. For example, a first template 14 may contain a set of markings 16 corresponding to a first compression level or profile, while a second template 14 may contain a set of markings 16 corresponding to a second compression level or profile. In the illustrated embodiments, the markings 16 on the template 14 of FIG. 14 are closer to the center 74 or interior 74 of the template 14 than the markings on the template 14 of FIG. 13. Accordingly, for a given patient, compression garment 12, and securement overlap, the template 14 of FIG. 14 may produce a garment 12 exhibiting greater compression than the template 14 of FIG. 13.

The fabrics, substrates, materials, or the like used to form a compression garment 12 may vary between embodiments. In selected embodiments, compression material used in a compression garment 12 may be a short-stretch fabric with maximum elastic elongation of about 15% to about 100% of an unstretched length. As the short stretch material nears its elastic limit, it may exhibit a fairly abrupt end-stretch or lock-out. The compression material may alternatively be a medium stretch or non-elastic fabric. In other embodiments, compression material used in a compression garment 12 may be "non-elastic" fabric having have less than about 15% maximal elastic stretch or no stretch at all.

Compression material used in a compression garment 12 may be a non-woven, woven, knitted, spacer-fabric, or a combination of fabric with lamination. The compression material may be a fabric laminated to foam, polyurethane, another fabric, or a combination of non-woven and woven or knitted fabrics. In certain embodiments, the compression material may be constructed by laminating two fabrics using foam or polyurethane coating between the layers, or other lamination techniques as known in the art. The compression garment may contain multiple fabric types, with various levels of maximum elastic stretch, various compression levels, or combinations thereof for any given fabric elongation.

The compression fabric may be selected based on a patient's measurements or measurement range, a desired therapeutic compression, or the like. The compression fabric may be reusable, somewhat reusable, or disposable. For example, compression fabric may comprise a disposable material designed for single use (e.g., nonwoven diaper-like material, nonwoven elastic bandage compression material, disposable multiple layer compression bandage material, or the like). Selected nonwoven materials suitable for use in embodiments in accordance with the present invention may include polyester fabric containing longitudinal strands of polyester urethane or similar elastomeric fibers. Such polyester fabric may be coated with a cohesive or adhesive substance. Alternatively, or in addition thereto, such fabrics may be compatible with hook-and-loop type fasteners (e.g., engage hook material urged thereagainst).

Embodiments in accordance with the present invention may include a series of templates 14. An appropriate template 14 may be selected based on the limb involved (e.g., foot, hand, leg, arm, abdomen, or the like), limb measurements (e.g., limb length, height, circumference, or the like), limb size (e.g., XS, S, M, L, XL, XXL), limb geometry or shape, desired compression levels, desired fabric stretch once a garment 12 donned, or the like. The chosen template 14 may be paired with a chosen or corresponding compression garment 12. The compression garment 12 may be selected based on the nature of the limb involved, limb geometry or shape, desired compression level, degree of fabric stretch, color, texture, or the like. The chosen template 14 may then be used with the chosen compression garment 12 and the patient measurements to trim the compression garment 12 in order to fit the patient. The trimmed garment 12 may then be applied to the patient and provide therapeutic compression.

A template 14 may be disposable or re-usable and constructed of paper, plastic, metal, cardboard, foamboard, or the like. A template 14 may have similar stretch to a corresponding compression fabric, so that it can be properly proven on the limb or body section prior to trimming the actual material of a compression garment 12. A template 14 may alternatively comprise an electronic file. For example, a template 14 may be a image generated by an electronic file and projected onto a compression garment 12.

In selected embodiments, a selection may be made based on desired features of a corresponding compression garment 12 (e.g., limb at issue, limb, size, closed toe, open toe, wide band at top, desired compression levels, etc.). A user may then collect various measurements from a patient (e.g., himself or herself) and enter them into a computer program (e.g., a program accessed over the Internet). A computer program may then generate an intermediate template 14 that may be printed or projected onto a template substrate (e.g., material used to form a final or usable template 14). When completed, the template 14 (e.g., the final or usable template 14) may be used to trim a corresponding compression garment 12. Alternatively, a computer program may generate a template 14 that may be printed or projected directly onto a corresponding compression garment 12 to assist in proper trimming of the garment 12.

In view of the foregoing, a therapeutic compression apparatus may comprise (1) a compression garment wrappable circumferentially about a limb of a patient and (2) at least one template comprising markings showing where to trim the compression garment to enable the compression garment to deliver a particular therapeutic compression profile to the limb. The at least one template may comprise a shape matching the compression garment.

The matching shape may enable a user to align the at least one template with respect to the compression garment. For example, the compression garment may comprise a garment perimeter. The at least one template may comprise a first template having a template perimeter. The template perimeter may match the entire garment perimeter. Alternatively, the template perimeter may match a portion of the garment perimeter, wherein the portion is sufficient to definitely and uniquely align the first template with respect to the compression garment. The at least one template may comprise paper with the markings printed thereon.

A first template of the at least one template may comprise markings enabling customization of the compression garment to deliver a first compression profile. A second template of the at least one template may comprise markings enabling customization of the compression garment to deliver a second compression profile, distinct from the first compression profile. A third template of the at least one template may comprise markings enabling customization of the compression garment to deliver a third compression profile, distinct from both the first and second compression profiles.

The compression garment may further comprise one or more bands positioned to wrap circumferentially about the limb of the patient. The markings may identify locations for trimming the one or more bands to shorten a circumferential reach thereof. The markings may provide a compressed scale taking into account the degree of stretch at application of the compression garment. The markings may include a plurality of numbers and a plurality of trim lines. Each number of the plurality of numbers may be positioned adjacent a corresponding trim line of the plurality of trim lines. The numbers may corresponding to measurements collected from the limb.

The compression garment of the therapeutic compression apparatus presented above may comprise short stretch material having a maximum elasticity of 15 to 100 percent under reasonable tensile loads. Reasonable tensile loads may be applied to a particular band of the compression garment and have a magnitude between about 2 lbs and about 20 lbs.

The therapeutic compression apparatus presented above may further comprise instructions instructing how to custom fit the compression garment to the patient, the instructions comprising (1) a first instruction to obtain a measurement of the circumference of the limb at a point and (2) a second instruction to cut the compression garment at a marking of the markings corresponding to the measurement.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of treating a condition of a patient's limb, the method comprising:
    obtaining a compression garment comprising
        a sheet of material wrappable about a limb of a patient,
        a first plurality of markings corresponding to the sheet,
        a second plurality of markings corresponding to the sheet,
        the first plurality of markings, wherein each marking thereof comprises a number and shows where to cut the sheet to deliver, for a given overlap of the sheet upon itself, a first particular compression to a portion of the limb having a circumference corresponding to the number, and
        the first plurality of markings, wherein the it particular compression for each of the first plurality of markings is in a first range selected from the group consisting of 8-15 mmHg, 15-20 mmHg, 20-30 mmHg, 30-40 mmHg, and 40-50 mmHg,
        the second plurality of markings, wherein each marking thereof comprises a number and shows where to cut the sheet to deliver, for the given overlap of the sheet upon itself, a second particular compression to a portion of a limb having a circumference corresponding to the number; and
        the second plurality of markings, wherein the second particular compression for each of the second plurality of markings is in a second range, distinct from the first range, selected from the group consisting of 8-15 mmHg, 15-20 mmHg, 20-30 mmHg, 30-40 mmHg, and 40-50 mmHg;
    taking a measurement of a circumference of the limb; and
    cutting the compression garment along a marking of one of the first plurality of markings and the second plurality of markings that matches the measurement.

2. The method of claim 1, wherein the material comprises short stretch material having an appreciable end stretch after an elongation in the range of 15 to 100 percent.

3. The method of claim 1, wherein the compression garment comprises non-elastic material, short stretch material, moderate stretch material, or long stretch material.

4. The method of claim 1, further comprising donning, by the patient after the cutting, the compression garment.

5. The method of claim 4, further comprising providing, by the compression garment after the donning, therapeutic compression to the limb.

6. The method of claim 4, wherein the donning comprises applying at least a portion of the compression garment at substantially end stretch.

7. The method of claim 1, wherein at least one of the first and second plurality of markings is on a template.

8. The method of claim 1, further comprising overlaying, prior to the cutting, at least a portion of the compression garment with the template.

9. The method of claim 1, wherein the compression garment further comprises:
    an upper band;
    lower bands; and
    an attachment mechanism attaching the upper band to the lower bands.

10. The method of claim 9, further comprising cutting away, prior to the donning, the upper band by trimming the attachment mechanism.

11. A therapeutic compression garment system comprising:
    a sheet of material wrappable about a limb;
    a first plurality of markings corresponding to the sheet;
    a second plurality of markings corresponding to the sheet;
    the first plurality of markings, wherein each marking thereof comprises a number and shows where to cut the sheet to deliver, for a given overlap of the sheet upon itself, a first particular compression to a portion of the limb having a circumference corresponding to the number;
    the first plurality of markings, wherein the first particular compression for each of the first plurality of markings is in a first range selected from the group consisting of 8-15 mmHg, 15-20 mmHg, 20-30 mmHg, 30-40 mmHg, and 40-50 mmHg;
    the second plurality of markings, wherein each marking thereof comprises a number and shows where to cut the sheet to deliver, for the given overlap of the sheet upon itself, a second particular compression to a portion of a limb having a circumference corresponding to the number; and
    the second plurality of markings, wherein the second particular compression for each of the second plurality of markings is in a second range, distinct from the first range, selected from the group consisting of 8-15 mmHg, 15-20 mmHg, 20-30 mmHg, 30-40 mmHg, and 40-50 mmHg.

12. The system of claim 11, wherein the material is short stretch material having an appreciable end stretch after an elongation in the range of 15 to 100 percent.

13. The system of claim 11, wherein the material is non-elastic material, short stretch material, moderate stretch material, or long stretch material.

14. The system of claim 11, wherein at least one of the first and second plurality of markings is on the material.

15. The system of claim 11, wherein at least one of the first and second plurality of markings is on a template.

16. The system of claim 15, further comprising overlaying, prior to the cutting, at least a portion of the compression garment with the template.

17. A method of treating a condition of a patient's limb, the method comprising:
- receiving, at a site, a patient suffering from at least one of lymphedema and venous insufficiency;
- obtaining, at the site, a compression garment comprising
   - a sheet of material wrappable about a limb of the patient,
   - a first plurality of markings corresponding to the sheet,
   - a second plurality of markings corresponding to the sheet,
   - the first plurality of markings, wherein each marking thereof comprises a number and shows where to cut the sheet to deliver, for a given overlap of the sheet upon itself, a first particular compression to a portion of the limb having a circumference corresponding to the number, and
   - the first plurality of markings, wherein the first particular compression for each of the first plurality of markings is in a first range selected from the group consisting of 8-15 mmHg, 15-20 mmHg, 20-30 mmHg, 30-40 mmHg, and 40-50 mmHg,
   - the second plurality of markings, wherein each marking thereof comprises a number and shows where to cut the sheet to deliver, for the given overlap of the sheet upon itself, a second particular compression to a portion of a limb having a circumference corresponding to the number; and
   - the second plurality of markings, wherein the second particular compression for each of the second plurality of markings is in a second range, distinct from the first range, selected from the group consisting of 8-15 mmHg, 15-20 mmHg, 20-30 mmHg, 30-40 mmHg, and 40-50 mmHg;
- taking, at the site, a measurement of a circumference of the limb; and
- cutting, at the site, the compression garment along a marking of one of the first plurality of markings and the second plurality of markings that matches the measurement.

18. The method of claim 17, wherein the obtaining comprises obtaining the compression garment further comprising an attachment mechanism.

19. The method of claim 17, further comprising, donning by the patient at the site, the compression garment by wrapping the sheet around the limb and using the attachment mechanism to maintain the sheet wrapped around the limb.

20. The method of claim 17, wherein the site is a hospital, medical clinic, or place of business of a supplier or distributor of durable medial equipment.

\* \* \* \* \*